United States Patent [19]
Nudelman et al.

[11] Patent Number: 6,030,961
[45] Date of Patent: Feb. 29, 2000

[54] OXYALKYLENE PHOSPHATE COMPOUNDS AND USES THEREOF

[75] Inventors: Abraham Nudelman, Rehovot, Israel; Ada Rephaeli, North Caldwell, N.J.

[73] Assignees: Bar-Ilan Research & Development Co., Ltd., Ramat-Gan; Mor Research Applications Ltd., Givat Shmuel, both of Israel

[21] Appl. No.: 08/814,386

[22] Filed: Mar. 11, 1997

[51] Int. Cl.[7] .............................. A61K 31/66; C07F 9/09; C07F 9/165

[52] U.S. Cl. ......................... 514/120; 514/121; 558/179; 558/180; 558/182

[58] Field of Search .................................. 558/179, 180, 558/182; 514/120, 121

[56] References Cited

U.S. PATENT DOCUMENTS

| | | | |
|---|---|---|---|
| 2,940,855 | 6/1960 | Beavers et al. | 96/107 |
| 3,219,630 | 11/1965 | Sidi | 260/67 |
| 3,293,220 | 12/1966 | Minami et al. | 260/67 |
| 3,336,262 | 8/1967 | Sidi | 260/67 |
| 3,720,706 | 3/1973 | Lapporte et al. | 260/494 |
| 3,812,176 | 5/1974 | Lapporte et al. | 260/494 |
| 3,931,412 | 1/1976 | Kensler, Jr. et al. | 424/313 |
| 3,980,738 | 9/1976 | Arlt et al. | 558/117 |
| 4,012,526 | 3/1977 | Kensler, Jr. et al. | 424/313 |
| 4,105,681 | 8/1978 | Bollag et al. | 260/404 |
| 4,123,552 | 10/1978 | Kensler, Jr. et al. | 424/311 |
| 4,198,416 | 4/1980 | Koeda et al. | 424/266 |
| 4,215,215 | 7/1980 | Bollag et al. | 542/427 |
| 4,541,944 | 9/1985 | Sanderson | 252/95 |
| 4,545,784 | 10/1985 | Sanderson | 8/107 |
| 4,613,505 | 9/1986 | Mizushima et al. | 424/80 |
| 4,699,925 | 10/1987 | Uchida et al. | 514/559 |
| 4,760,057 | 7/1988 | Alexander | 514/187 |
| 4,816,570 | 3/1989 | Farquhar | 536/27 |
| 4,885,311 | 12/1989 | Parish et al. | 514/549 |
| 4,900,478 | 2/1990 | Gross | 260/408 |
| 4,916,230 | 4/1990 | Alexander | 546/318 |
| 4,968,788 | 11/1990 | Farquhar | 536/27 |
| 5,025,029 | 6/1991 | Perrine | 514/381 |
| 5,158,773 | 10/1992 | Gross | 424/401 |
| 5,185,436 | 2/1993 | Villa et al. | 536/4.1 |
| 5,196,567 | 3/1993 | Uchida et al. | 560/102 |
| 5,200,553 | 4/1993 | Nudelman et al. | 560/263 |
| 5,216,004 | 6/1993 | Perrine | 514/381 |
| 5,569,675 | 10/1996 | Rephaeli et al. | 514/547 |
| 5,710,176 | 1/1998 | Rephaeli et al. | 514/548 |

FOREIGN PATENT DOCUMENTS

| | | |
|---|---|---|
| 0 056 189 A1 | 7/1982 | European Pat. Off. |
| 0 167 204 B1 | 1/1986 | European Pat. Off. |
| 0 371 789 A2 | 6/1990 | European Pat. Off. |
| 1 386 096 | of 1965 | France |
| 1 540 418 | 9/1968 | France |
| 58-15912 | 1/1983 | Japan |
| 63-101348 | 5/1988 | Japan |
| 1177442 | 1/1970 | United Kingdom |
| 1 220 447 | 1/1971 | United Kingdom |
| 1382010 | 1/1975 | United Kingdom |
| 2126082 | 3/1984 | United Kingdom |
| WO93/19778 | 10/1993 | WIPO |

OTHER PUBLICATIONS

Nehring, Chemical Abstracts, vol. 66, abstract 18253, 1967.

Srivastva et al., Chemical Abstracts, vol. 113, abstract 152924, 1990.

Farquhar et al., Chemical Abstracts, vol. 122, abstract 10455, 1995.

Farquhar et al., Chemical Abstracts, vol. 122, abstract 133667, 1995.

Casagrande et al., Chemical Abstracts, vol. 105, abstract 97679, 1986.

Bednarski, et al., "Rabbit Muscle Aldolase as a Catalyst in Organic Synthesis", Chem. Abstracts, vol. 110, Abstract 57935c, 1989.

Bhatia, et al., "Induction of Cell Differentiation Potentiates Apoptosis Triggered by Prior Exposure to DNA–damaging Drugs", Cell Growth and Differentiation, vol. 6, pp. 937–944, 1995.

Boffa, et al., "Manifold Effects of Sodium Butyrate on Nuclear Function", J. Biol. Chem., vol. 256, No. 18, pp. 9612–9621, 1981.

Bourgeade, et al., "Reorganization of the Cytoskeleton by Interferon in MSV–Transformed Cells", J. of Interferon Res., vol. 1, No. 2, pp. 323–332, 1981.

Brant and Conklin, "Acrolein Diacylates", Chem. Abstracts, vol. 40, p. 3127, 1946.

Carstea, et al., "Analogues of Butyric Acid that Increase the Expression of Transfected DNAs", Biochem. Biophys. Res. Com., vol. 192, No. 2, pp. 649–656, 1993.

Cheng, et al., "Functional Activation of the Cystic Fibrosis Trafficking Mutant deltaF508–CFTR by Overexpression", American Journal of Physiology, vol. 268, No. 4, pp. L615–L624, 1995.

Conway, et al., "Induction of Apoptosis by Sodium Butyrate in the Human Y–79 Retinoblastoma Cell Line", Oncology Research, vol. 7, No. 6, pp. 289–297, 1995.

(List continued on next page.)

*Primary Examiner*—Richard L. Raymond
*Attorney, Agent, or Firm*—Kenyon & Kenyon

[57] ABSTRACT

This invention relates to compositions for and methods of treating, preventing or ameliorating cancer and other proliferative diseases as well as methods of inducing wound hearing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, modulating gene expression and in particular, augmenting expression of tumor suppressor genes, inducing tolerance to antigens, treating, preventing or ameliorating protozoan infection, or inhibiting histone deacetylase in cells. The compositions of the invention are to and the methods of the invention use oxyalkalene phosphate compounds.

52 Claims, 4 Drawing Sheets

OTHER PUBLICATIONS de Haan, et al., "Effects of Sodium Butyrate on the Synthesis and Methylation of DNA in Normal Cells and Their Transformed Counterparts", Cancer Res., vol. 46, No. 2, pp. 713–716, 1986.

Farquhar, et al., "Biologically Reversible Phosphate Protective Groups", J. Pharm. Sci., vol. 72, No. 3, pp. 324–325, 1983.

Farquhar, et al., "Synthesis and Antitumor Evaluation of Bis[(pivaloyloxy)methyl]2'–Deoxy–5–fluorouridine 5'-Monophosphate (FdUMP): A Strategy to Introduce Nucleotides into Cells", J. Med. Chem., vol. 37, No. 23, pp. 3902–39009, 1994.

Fishman and Atikkan, "Induction of Cholera Toxin Receptors in Cultured Cells by Butyric Acid", J. Biol. Chem., vol. 254, No. 11, pp. 4342–4344, 1979.

Friis and Bundgaard, "Prodrugs of phosphates and phosphonates: Novel lipophilic alpha–acyloxyalkyl ester derivatives of phosphate– or phosphonate containing drugs masking the negative charges of these groups", Eur. J. Pharm. Sci., vol. 4, pp. 49–59, 1996.

Hague, et al., "Apoptosis in Colorectal Tumor Cells: Induction by the Short Chain Fatty Acids Butyrate, Propionate and Acetate and by the Bile Salt Deoxycholate", Int. J. Cancer, vol. 60, pp. 400–406, 1995.

Ingram and Thomas, "The Electron Impact Induced Fragmentation of Geminal Dialkanoates", Organic Mass Spectrometry, vol. 12, No. 4, pp. 216–221, 1977.

Man, et al., "Boron Fluoride Catalyzed Addition of Aliphatic Anhydrides to Aldehydes", J. Am. Chem. Soc., pp. 847–848, 1950.

Miller, et al., "Clinical Pharmacology of Sodium Butyrate in Patients with Acute Leukemia", Eur. J. Cancder Clin Oncol. vol. 23, No. 9, pp. 1283–1287, 1987.

Mosher and Kehr, "The Oxidation of Aliphatic Esters with Lead Tetraacetate", J. Am. Chem. Soc., vol. 82, pp. 5342–5345, 1960.

Nielsen and Bundgaard, "Evaluation of Glycolamide Esters and Various Other Esters of Aspirin as True Aspirin Prodrugs", J. Medicinal Chem., vol. 32, pp. 727–734, 1989.

Nordenberg, et al., "Growth Inhibition of Murine Melanoma by Butyric Acid and Dimethylsulfoxide", Exp. Cell Res., vol. 162, pp. 77–85, 1986.

Nordenberg,, et al., "Biochemical and Ultrastructural Alterations Accompany the Anti–proliferative Effect of Butyrate on Melanoma Cells", Br. J. Cancer, vol. 55, pp. 493–497, 1987.

Novogrodsky, et al., "Effect of Polar Organic Compounds on Leukemic Cells", Cancer, vol. 51, No. 1, pp. 9–14, 1983.

Nudelman, et al., "Novel Anticancer Prodrugs of Butyric Acid", J. Med. Chem., vol. 35, pp. 687–694, 1992.

Oh, et al., "Convenient Synthesis of Geminal Biscarboxylates:Searching for an Efficient Route to HR 916B", Korean J. Med. Chem., vol. 6, No. 2, pp. 259–262, 1996.

Prasad, "Butyric Acid; A Small Fatty Acid with Diverse Biological Functions", Life Sci., vol. 27, No. 15, pp. 1351–1358, 1980.

Prasad, et al., "Decreased Expressions of c–myc and H–ras Oncogenes in Vitamin E Succinate Induced Morphologically Differentiated Murine B–16 Melanoma Cells in Culture", Biochem. Cell Bio., vol. 68, No. 11, pp. 1250–1255, 1990.

Rabizadeh, et al., "Rapid Alteration of c–myc and c–jun Expression in Leukemic Cells Induced to Differentiate By a Butyric Acid Prodrug", FEBS Lett., vol. 328, No. 3, pp. 225–229, 1993.

Rephaeli, et al., "Butyrate–Induced Differentiation in Leukemic Myeloid Cells: in vitro and in vivo Studies", International Journal of Oncology, vol. 4, No. 6, pp. 1387–1391, 1994.

Riggs, et al., "n–Butyrate Causes Histone Modification in HeLa and Friend Erythroleukaemia Cells", Nature, vol. 268, No. 5617, pp. 462–464, 1977.

Safadi, et al, "Phosphoryloxymethyl Carbamates and Carbonates– Novel Water–Soluble Prodrugs for Amines and Hindered Alcohols", Pharm. Res., vol. 10, No. 9, pp. 1350–1355, 1993.

Sagawa, et al., "Agricultural Chemicals Based on Dialkyl Halomethyl Phosphates for Killing Insects, Worms and Bacteria", Chem. Abstracts, vol. 78, Abstract #132708g, 1973.

Samid, et al., "Phenylacetate: A Novel Nontoxic Inducer of Tumor Cell Differentiation", Cancer Res., vol, 52, No. 7, pp. 1988–1992, 1992.

Sher, et al., "Extended Therapy with Intravenous Arginine Butyrate in Patients with Beta–Hemoglobinopathies", New England Journal of Medicine, vol. 332, No. 24, pp. 1606–1610, 1995.

Smigel, "Nontoxic Drug Being Tested to Treat Cancer and Anemias", J. Nat'l Cancer Inst., vol. 84, No. 18, pp. 1398–1399, 1992.

Smith, et al., "Incorporation of Tributyrin Enhances the Expression of a Reporter Gene in Primary and Immortalized Cell Lines", Biotechniques, vol. 18, No. 5, pp. 852–855, 1995.

Srivastva and Farquhar, "Bioreversible Phosphate Protective Groups: Synthesis and Stability of Model Acyloxymethyl Phosphates", Bioorganic Chemistry, vol. 12, pp. 118–129, 1984.

Srivastva, et al., "Mass Spectral Characterization of Acyloxymethyl Phosphates", J. Chem. Tech. Biotechnol., vol. 47, pp. 235–243, 1990.

Stamatoyannopoulos, et al., "Therapeutic Approaches to Hemoglobin Switching in Treatment of Hemoglobinopathies", Ann. Rev. Med., vol. 43, pp. 497–522, 1992.

Tang, et al., "Butyrate–Inducible and Tumor–Restricted Gene Expression by Adenovirus Vectors", Cancer Gene Therapy, vol. 1, No. 1, pp. 15–20, 1994.

Thorne, et al., "Patterns of Histone Acetylation", Eur. J. Biochem., vol. 193, pp. 701–713, 1990.

Tomiska and Spousta, "Low–Molecular Polyoxymethylene Diacetates from Trioxane", Angew. Chem. Internat. Edit., vol. 1, No. 4, p. 211, 1962.

Toscani, et al., "Molecular Analysis of Sodium Butyrate–Induced Growth Arrest", Oncogene Res., vol. 3, No. 3, pp. 223–238, 1988.

THE EFFECT OF AB AND BODP ON THE CLONOGENICITY OF NEUROBLASTOMA CELL LINES SK-N-SH

THE EFFECT OF AB AND BODP ON THE CLONOGENICITY OF NEUROBLASTOMA CELL LINES NBAS-5

THE EFFECT OF BODP ON THE EXPRESSION OF CD11b
IN HUMAN PROMYELOCYTIC LEUKEMIC CELL LINE --- HL-60

OXYALKYLENE PHOSPHATE COMPOUNDS AND USES THEREOF

FIELD OF THE INVENTION

This invention relates to compounds, compositions and methods for treating, preventing or ameliorating cancer and other proliferative diseases as well as methods of inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially HBV-associated tumors, modulating gene expression and particularly augmenting expression of tumor suppression genes, inducing tolerance to antigens, treating or preventing parasitic infections and inhibiting histone deacetylase in cells. The methods of the invention use oxyalkylene phosphate compounds.

BACKGROUND OF THE INVENTION

Butyric acid (BA) is a natural product. It is supplied to mammals from two main sources: 1) the diet, mainly from dairy fat, and 2) from the bacterial fermentation of unabsorbed carbohydrates in the colon, where it reaches mM concentrations (Cummings, *Gut* 22:763–779, 1982; Leder et al., *Cell* 5:319–322, 1975).

BA has been known for nearly the last three decades to be a potent differentiating and antiproliferative agent in a wide spectrum of neoplastic cells in vitro (Prasad, *Life Sci.* 27:1351–1358, 1980). In cancer cells, BA has been reported to induce cellular and biochemical changes, e.g., in cell morphology, enzyme activity, receptor expression and cell-surface antigens (Nordenberg et al., *Exp. Cell Res.* 162:77–85, 1986; Nordenberg et al., *Br. J. Cancer* 56:493–497, 1987; and Fishman et al., *J. Biol. Chem.* 254:4342–4344, 1979).

Although BA or its sodium salt (sodium butyrate, SB) has been the subject of numerous studies, its mode of action is unclear. The most specific effect of butyric acid is inhibition of nuclear deacetylase(s), resulting in hyperacetylation of histones H3 and H4 (Riggs, et al., *Nature* 263:462–464, 1977). Increased histone acetylation following treatment with BA has been correlated with changes in transcriptional activity and the differentiated state of cells (Thome et al., *Eur. J. Biochem.* 193:701–713, 1990). BA also exerts other nuclear actions, including modifications in the extent of phosphorylation (Boffa et al., *J. Biol. Chem.* 256:9612–9621, 1981) and methylation (Haan et al., *Cancer Res.* 46:713–716, 1986). Other cellular organelles, e.g., cytoskeleton and membrane composition and function, have been shown to be affected by BA (Bourgeade et al., *J. Interferon Res.* 1:323–332, 1981). Modulations in the expression of oncogenes and suppressor genes by BA were demonstrated in several cell types. Toscani et al., reported alterations in c-myc, p53 thymidine kinase, c-fos and AP2 in 3T3 fibroblasts (*Oncogene Res.* 3:223–238, 1988). A decrease in the expression of c-myc and H-ras oncogenes in B16 melanoma and in c-myc in HL-60 promyelocytic leukemia was also reported (Prasad et al., *Biochem. Cell Biol.* 68:1250–1255, 1992; and Rabizadeh et al., *FEBS Lett.* 328:225–229, 1993).

BA has been reported to induce apoptosis, i.e., programmed cell death. SB has been shown to produce apoptosis in vitro in human colon carcinoma, leukemia and retinoblastoma cell lines (Bhatia et al., *Cell Growth Diff.* 6:937–944, 1995; Conway et al., *Oncol. Res.* 7:289–297, 1993; Hague et al.; *Int J. Cancer* 60:400–406, 1995). Apoptosis is the physiological mechanism for the elimination of cells in a controlled and timely manner. Organisms maintain a delicate balance between cell proliferation and cell death, which when disrupted can tip the balance between cancer, in the case of over accumulation of cells, and degenerative diseases, in the case of premature cell losses. Hence, inhibition of apoptosis can contribute to tumor growth and promote progression of neoplastic conditions.

The promising in vitro antitumor effects of BA and BA salts led to the initiation of clinical trials for the treatment of cancer patients with observed minimal or transient efficacy. [Novogrodsky et al., *Cancer* 51:9–14, 1983; Rephaeli et al., *Intl. J. Oncol.* 4:1387–1391, 1994; Miller et al., *Eur. J. Cancer Clin. Oncol.* 23:1283–1287, 1987].

Clinical trials have been conducted for the treatment of β-globin disorders (e.g., β-thalassemia and sickle-cell anemia) using BA salts. The BA salts elevated expression of fetal hemoglobin (HbF), normally repressed in adults, and favorably modified the disease symptoms in these patients (Stamatoyannopouos et al., *Ann. Rev. Med.* 43:497–521, 1992). In this regard, arginine butyrate (AB) has been used in clinical trials with moderate efficacy (Perrine et al, *N. Eng. J. Med.* 328:81–86, 1993; Sher et al, *N. Eng. J. Med.* 332:1606–1610, 1995). The reported side effects of AB included hypokalemia, headache, nausea and vomiting in β-thalassemia and sickle-cell anemia patients.

Butyric acid derivatives with antitumor activity and immunomodulatory properties have been reported in U.S. Pat. No. 5,200,553 and by Nudelman et al, 1992, *J. Med. Chem.* 35:687–694. The most active butyric acid prodrug reported in these references was pivaloyloxymethyl butyrate (AN-9). None of the compounds disclosed in these references included carboxylic acid-containing oxyalkyl compounds of this invention.

BA and/or its analogues have also been reported to increase the expression of transfected DNA (Carstea et al., 1993, *Biophys. Biohem. Res. Comm.* 192:649; Cheng et al., 1995, *Am. J. Physical* 268:L615–L624) and to induce tumor-restricted gene expression by adenovirus vectors (Tang et al., 1994, *Cancer Gene Therapy* 1:15–20). Trbutyrn has been reported to enhance the expression of a reporter gene in primary and immortalized cell lines (Smith et al., 1995, *Biotechniques* 18:852–835).

Butyric acid derivatives with antitumor activity and immunomodulatory properties have been reported in U.S. Pat. No. 5,200,553 and by Nudelman et al., 1992, *J. Med. Chem.* 35:687–694. The most active buryric acid prodrug reported in these references was pivaloyloxymethyl butyrate (AN-9). Similar compounds are reported for treating hemoglobinopathies (U.S. Pat. No. 5,569,675).

BA and/or its analogues have also been reported to increase the expression of transfected DNA (Carstea et al., 1993, *Biophys. Biohem. Res. Comm.* 192:649; Cheng et al., 1995, *Am. J. Physical* 268:L615–L624) and to induce tumor-restricted gene expression by adenovirus vectors (Tang et al., 1994, *Cancer Gene Therapy* 1:15–20). Tributyrin has been reported to enhance the expression of a reporter gene in primary and immortalized cell lines (Smith et al., 1995, *Biotechniques* 18:852–835).

However, BA and its salts are normally metabolized rapidly and have very short half-lives in vivo, thus the achievement and maintenance of effective plasma concentrations are problems associated with BA and BA salts, particularly for in vivo uses. BA and BA salts have required large doses to achieve even minimal therapeutic effects. Because of the high dosage, fluid overload and mild alkalosis may occur. Patients receiving BA emanate an unpleasant odor that is socially unacceptable.

While BA salts have been shown to increase HbF expression, and appear to hold therapeutic promise with low toxicity in cancer patients, they nevertheless have shown low potency in in vitro assays and clinical trials. There also remains a need to identify compounds as effective or more effective than BA or BA salts as differentiating or anti-proliferating agents for the treatment of cancers. Such compounds need to have higher potency than BA without the problems associated with BA (such as bad odor). Consequently, there remains a need for therapeutic compounds that either deliver BA to cells in a longer acting form or which have similar activity as BA but a longer duration of effectiveness in vivo.

The compounds and compositions of this invention address these needs and are more potent than BA or BA salts for treating cancers and other proliferative diseases, for treating gastrointestinal disorders, for wound healing and for treating blood disorders such as thalassemia, sickle cell anemia and other anemias, for modulating an immune response, for enhancing recombinant gene expression, for treating insulin-dependent patients, for treating cystic fibrosis patients, for inhibiting telomerase activity, for detecting cancerous or malignant cells, for treating virus-associated tumors, especially EBV-associated tumors, for modulating gene expression and particularly for augmenting expression of a tumor suppressor gene, inducing tolerance to an antigen, treating, preventing or ameliorating parasitic infection and inhibiting histone deacetylase in cells. One of the advantages of the compounds of the invention is increased water solubility of the free carboxylic acids compounds of the invention and their salts, and easier administration, especially for intravenous administration.

SUMMARY OF THE INVENTION

Accordingly, in one embodiment of the present invention there is provided a method of treating, preventing or ameliorating cancer and other proliferative disorders using compounds having the Formula I:

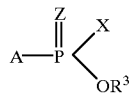

wherein

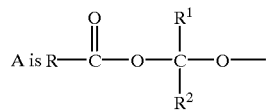

and wherein

R is $C_1$–$C_{10}$ alkyl, $C_2$–$C_{10}$ alkenyl or $C_2$–$C_{10}$ alkynyl each optionally substituted withat least one amino, acylamino, halo, trifluoromethyl, hydroxy, alkoxy, alkyl, carbonyl, aryl, heteroaryl, substituted heteroaryl group or combination thereof;

$R^1$ and $R^2$ are each independently H or $C_1$–$C_6$ alkyl, $C_2$–$C_6$ alkenyl or $C_2$–$C_6$ alkynyl wherein the alkyl, alkenyl or alkyknyl group or combination thereof is optionally substituted with halo or alkoxy; and Z is oxygen or sulfur, with the proviso that when Z is oxygen X is $R^4$ or $OR^5$;

$R^3$ and $R^5$ are both H or each is independently $C_1$–$C_6$ alkyl, alkenyl, alkynyl, aralkyl, aryl, heteroaryl or heteroaralkyl;

$R^4$ is $C_1$–$C_6$ alkyl, alkenyl, alkynyl, aralkyl, aryl, heteroaryl or heteroaralkyl; and when Z is sulfur X is A, $R^4$ or $OR^5$;

$R^3$ and $R^5$ are each independently H, $C_1$–$C_6$ alkyl, alkenyl, alkynyl, aralkyl, aryl, heteroaryl or heteroaralkyl;

$R^4$ is $C_1$–$C_6$ alkyl, alkenyl, alkynyl, aralkyl, aryl, heteroaryl or heteroaralkyl, or both X and $OR^3$ are A.

In a preferred embodiment, the compound is as defined above wherein R is $C_3$ to $C_6$ alkyl or alkenyl, optionally substituted with halo, alkyl, aryl or heteroaryl. In another preferred embodiment, R of Formula I is propyl. In yet another preferred embodiment, $R^1$ is H or alkyl and $R^2$ is H.

The compounds of Formula I wherein A, R, $R^1$, $R^2$, $R^3$, $R^4$, $R^5$, X and Z are as defined above are particularly useful for methods of treating, preventing or ameliorating the effects of cancer and other proliferative disorders by acting as anti-proliferative or differentiating agents in subjects afflicted with such anomalies. Such disorders include but are not limited to leukemias, such as acute promyelocytic leukemia, acute myeloid leukemia, and acute myelomonocytic leukemia; other myelodysplastic syndromes, multiple myeloma such as but not limited to breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. It is also possible that compounds of Formula I as defined above have anti-proliferative effects on non-cancerous cells as well, and may be of use to treat benign tumors and other proliferative disorders such as psoriasis. Preferred is the method for treating or ameliorating leukemia, squamous cell carcinoma and neuroblastoma.

The invention is further directed to a method of treating blood disorders by administering to a patient a therapeutically-effective amount of a compound of Formula I as defined above. The blood disorders treatable in accordance with the invention include, but are not limited to, thalassemias, sickle cell anemias, infectious anemias, aplastic anemias, hypoplastic and hypoproliferative anemias, sideroblastic anemias, myelophthisic anemias, antibody-mediated anemias, anemias due to chronic diseases and enzyme-deficiencies, and anemias due to blood loss, radiation therapy and chemotherapy. In this regard, these methods can include increasing hemoglobin content in blood by adminstering to a patient a therapeutically-effective amount of a compound of Formula I as defined above.

Another embodiment of the invention is directed to a method of modulating an immune response in a host by administering an amount of a compound of Formula I as defined above effective to modulate said immune response. Modulation of the immune response includes enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, enhancing progenitor cell recovery after bone marrow transplantation and combinations thereof.

Another embodiment of the present invention is directed to methods of treating, preventing or ameliorating cancer and other proliferative disorders which comprise administering a therapeutically effective amount of a compound of Formula I as defined above to a subject suffering from such disorder, together with other known antiproliferative, differentiating or oncostatic pharmaceutical agent to thereby enhance the mode of action of these agents. The pharmaceutical agents of the invention for the above method include but are not limited to, cytokines, interleukins, anticancer agents, chemotherapeutic agents, antibodies, conjugated antibodies, immune stimulants, antibiotics, hormone antagonists, and growth stimulants. The compounds of the invention can be administered prior to, after or concurrently with any of the agents.

Yet another embodiment of the invention is directed to a method of ameliorating the effects of a cytotoxic agent which comprises adminstering a therapeutically-effective amount of a cytotoxic agent with a compound of Formula I as defined above to a mammalian patient for a time and in an amount to induce growth arrest of rapidly-proliferating epithelial cells of the patient and thereby protect those cells from the cytotoxic effects of the agent. The cytotoxic agent may be a chemotherapeutic agent, an anticancer agent, or radiation therapy. Rapidly proliferating epithelial cells are found in hair follicles, the gastrointestinal tract, and the bladder, for example. Such cells include hair follicle cells and intestinal cryt cells. Rapidly proliferating cells are also found in the bone marrow and include bone marrow stem cells. In accordance with the invention the cytotoxic agent and the compound of Formula I can be administered simultaneously, or the cytotoxic agent can be administered prior to or after the compound of the invention. Administration (simultaneously or separately) can be done systemically or topically as determined by the indication. In addition, when the cytotoxic agent is radiation therapy, the compound of the invention may be administered to a cancer patient pre- or post-radiation therapy to treat or ameliorate the effects of cancer.

A still further embodiment of the invention is directed to a method of inducing wound healing, treating cutaneous ulcers or treating a gastrointestinal disorder by administering a therapeutically-effective amount of a compound of Formula I as defined above to a subject in need of such treatment. The cutaneous ulcers which can be treated in accordance with the methods of the invention include leg and decubitus ulcers, stasis ulcers, diabetic ulcers and atherosclerotic ulcers. With respect to wound healing, the compounds are useful in treating abrasions, incisions, burns, and other wounds. Gastrointestinal disorders treatable by the methods of the invention include colitis, inflammatory bowel disease, Crohn's disease and ulcerative colitis.

A further embodiment of the invention relates to a method of enhancing recombinant gene expression by treating a recombinant host cell containing an expression system for a mammalian gene product of interest with an expression-enhancing amount of a compound of Formula I as defined above, wherein said gene product is encoded by a butyric acid-responsive gene. The host cells can be mammalian cells, insect cells, yeast cells or bacterial cells and the correspondingly known expression systems for each of these host cells. The gene product can be any protein or peptide of interest, expression of which can be regulated or altered by butyric acid or a butyric acid salt. A butyric acid-responsive gene is a gene that has a promoter, enhancer element or other regulon that modulates expression of the gene under its control in response to butyric acid or a salt of butyric acid. For example, gene products contemplated for regulation in accordance with the invention include but are not limited to tumor suppressor genes (such as p53) and the γ-globin chain of fetal hemoglobin.

Yet a further embodiment of the invention is directed to a method of treating, preventing or ameliorating symptoms in insulin-dependent patients by administering an amount of a compound of Formula I as defined above effective to enhance insulin expression.

Yet another embodiment of the invention relates to a method of treating, preventing or ameliorating symptoms in cystic fibrosis patients by administering an amount of a compound of Formula I as defined above effective to enhance chloride channel expression.

Still another method of the invention is directed to a method of inhibiting telomerase activity in cancer cells by administering a telomerase-inhibiting amount of a compound of Formula I as defined above to the cells, wherein the amount is effective to decrease the telomerase activity of the cells and thereby inhibit the malignant progression of the cells. This method can be applied in vivo or in vitro to cells.

Another embodiment of this invention is directed to a method of treating, preventing or ameliorating virus-associated tumors by pre-, post or co-administering a therapeutically-effective amount of a compound of Formula I as defined above with a therapeutically-effective amount of an antiviral agent. Antiviral agents contemplated for use in the invention include ganciclovir, acyclovir and famciclovir, and preferably ganciclovir. The virus-associated tumors which can be treated, prevented or ameliorated in accordance with the invention include, but are not limited to, EBV-associated malignancy, Kaposi's sarcoma, AIDS-related lymphoma, hepatitis B-associated malignancy or hepatitis C associated malignancy. EBV-associated malignancies include nasopharyngeal carcinoma and non-Hodgkins' lymphoma and are preferred embodiments of the invention.

Further still, the invention provides a method of modulating gene expression by treating a host or host cells with a compound of Formula I as defined above in an amount effective to enhance, augment or repress the expression of a gene of interest, preferably a butyric-acid responsive gene. When expression of the gene of interest is to be enhanced or augmented, the gene may encode a gene product which is or acts as a repressor of another gene, a tumor suppressor, an inducer of apoptosis or an inducer of differentiation. When expression of the gene of interest is to be repressed, the gene may encode a gene product which or acts as an oncogene or an inhibitor of apoptosis. For example, the Bcl-2 gene encodes an inhibitor of apoptosis.

More particularly, the invention is directed to a method of augmenting gene expression, especially of a tumor suppressor gene, a butyric acid-responsive gene or a fetal hemoglobin gene, by treating a host or host cells with an expression-enhancing amount of a compound of Formula I as defined above. Preferably the host is a cancer patient. This method of the invention thus includes augmenting tumor suppressor gene expression in conjunction with ex vivo or in vivo gene therapy, i.e., the compound of the invention can be co-administered to the host during administration of gene therapy vectors or administration of the ex vivo transfected cells. Similarly, the compounds of the invention can be used to treat cells during a transfection step of ex vivo gene therapy. The hosts of the method therefore include cancer patients or other patients under going gene therapy. The host cells of the invention include hematopoietic cells such as stem cells and progenitor cells, e.g., or any other cell type used in ex vivo gene therapy.

Yet another embodiment of the invention is directed to a method of inducing tolerance to an antigen which comprises administering a therapeutically-effective amount of compound of Formula I as defined above. Preferably the antigen is a self-antigen.

Yet further, the invention is directed to a method for treating, preventing, or ameliorating protozoan infection in a subject which comprises administering to said subject an effective amount of a compound of Formula I as defined above. The protozoan infections treatable in accordance with the invention include, but are not limited to, malaria, cryptosporidiosis, toxoplasmosis and coccidiosis.

Still further the invention is directed to a method of inhibiting histone deacetylase in cells which comprises administering an effective amount of a compound of Formula I as defined above to said cells.

Another embodiment of the present invention is drawn to pharmaceutical compositions comprising a therapeutically effective amount of a compound represented by the formula IA:

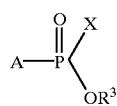

(Formula IA)

wherein A is

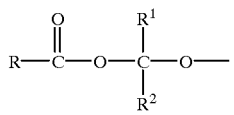

and wherein

R is $C_3$–$C_{10}$ straight chain alkyl, optionally substituted with one amino, acylamino, halo, trifluoromethyl, hydroxy, alkoxy, alkyl, carbonyl, aryl, heteroaryl or substituted heteroaryl group; or $C_2$–$C_{10}$ alkenyl or $C_2$–$C_{10}$ alkynyl, each optionally substituted withat least one amino, acylamino, halo, trifluoromethyl, hydroxy, alkoxy, alkyl, carbonyl, aryl, heteroaryl or substituted heteroaryl group;

$R^1$ and $R^2$ are each independently H or $C_1$–$C_6$ alkyl, $C_2$–$C_6$ alkenyl or $C_2$–$C_6$ alkynyl wherein the alkyl, alkenyl or alkyknyl group or combination thereof is optionally substituted with halo or alkoxy;

X is $R^4$ or $OR^5$, and $R^3$ and $R^5$ are both H or each is independently $C_1$–$C_6$ alkyl, alkenyl, alkynyl, aralkyl, aryl, heteroaryl or heteroaralkyl;

$R^4$ is $C_1$–$C_6$ alkyl, alkenyl, alkynyl, aralkyl, aryl, heteroaryl or heteroaralkyl;

with the proviso that when X is phenoxy, $R^3$ is benzyloxy and $R^1$ and $R^2$ are both hydrogen, then R is not methyl, isopropyl or tert-butyl; and when R is isopropyl, X is not phenoxy or $R^3$ is not benzyl; and a pharmaceutically acceptable carrier or diluent.

Preferred pharmaceutical compositions of the invention comprise a compound of Formula I as defined above, wherein R is $C_3$–$C_6$ alkyl or alkenyl, optionally substituted with halo, alkyl, aryl or heteroaryl; $R^1$ is H or alkyl and $R^2$ is H; X and $R^3$ are each independently alkyloxy, alkenyloxy, aryloxy, arylalkyloxy; and Z is oxygen; and pharmaceutically acceptable salts thereof. Particularly preferred compounds include butyroyloxymethyl diethyl phosphate, 1-(1-butyroyloxy)ethyl diethyl phosphate, mono (butyroyloxymethyl) phosphate, 1{1-(4-phenylbutyroyloxy) ethyl} diethyl phosphate and salts thereof.

Another embodiment of the present invention is directed to a pharmaceutical composition represented by the formula IB:

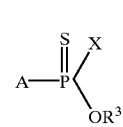

(Formula IB)

wherein A is

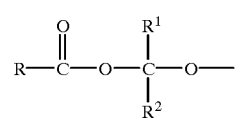

and wherein

R is $C_1$–$C_{10}$ alkyl, $C_2$–$C_{10}$ alkenyl or $C_2$–$C_{10}$ alkynyl, each optionally substituted withat least one amino, acylamino, halo, trifluoromethyl, hydroxy, alkoxy, alkyl, carbonyl, aryl, heteroaryl or substituted heteroaryl group;

$R^1$ and $R^2$ are each independently H or $C_1$–$C_6$ alkyl, $C_2$–$C_6$ alkenyl or $C_2$–$C_6$ alkynyl wherein the alkyl, alkenyl or alkynyl group or combination thereof is optionally substituted with halo or alkoxy;

X is A, $R^4$ or $OR^5$, wherein $R^3$ and $R^5$ both are H or each is independently $C_1$–$C_6$ alkyl, alkenyl, alkynyl, aryl, aralkyl, heteroaryl or heteroaralkyl;

$R^4$ is $C_1$–$C_6$ alkyl, alkenyl, alkynyl, aryl, aralkyl, heteroaryl or heteroaralkyl;

or both X and $OR^3$ are A;

A further embodiment of the present invention is directed to pharmaceutical compositions comprising a therapeutically effective amount of a compound of Formula IA or IB as defined above, together with other anti-cancer or antineoplastic agents and a pharmaceutically effective carrier or diluent.

DETAILED DESCRIPTION OF THE INVENTION

Figure 1A:
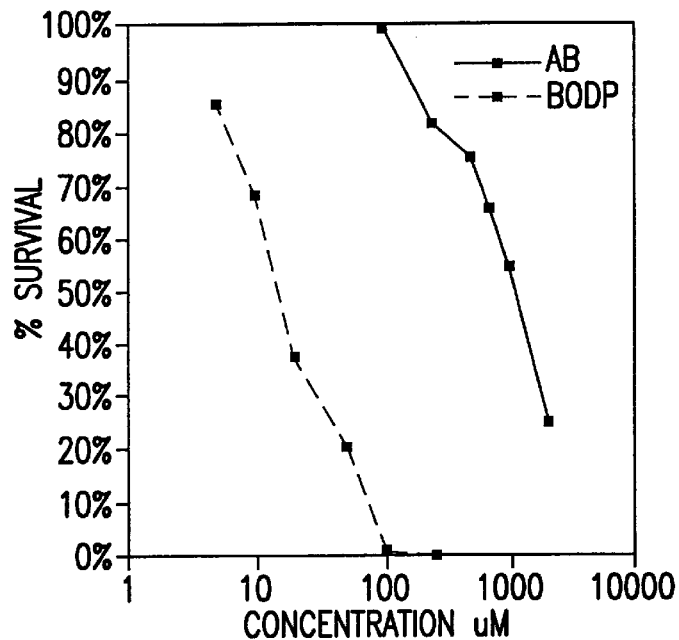
FIGS. 1A, 1B and 1C are graphic illustrations showing the in vitro inhibition of cellular growth (clonogenicity) of butyroyloxymethy diethyl phosphate (BODP) and butyric acid (AB) on proliferation of established human neuroblastoma cell lines SK-N-SH (FIG. 1A), NBAS-5 (FIG. 1B) and IMR-32 (FIG. 1C).

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein, "alkyl" means both branched- and straight-chain unless expressly stated otherwise, saturated aliphatic hydrocarbon groups having the specified number of carbon atoms. As used herein "lower alkyl" means an alkyl group having 1 to 5 carbon atoms. As used herein, "alkenyl" means hydrocarbon chains of either a straight or branched configuration and one or more unsaturated carbon-carbon bonds, such as ethenyl, propenyl, and the like. "Lower alkenyl" is an alkenyl group having 2 to 6 carbon atoms. As used herein, "alkynyl" means hydrocarbon chains of either a straight or branched configuration and one or more carbon-carbon triple bonds, such as ethynyl, propynyl and the like. "Lower alkynyl" is an alkynyl group having 2 to 6 carbon atoms. When the number of carbon atoms is not specified, then alkyl, alkenyl and alkynyl means lower alkyl, lower alkenyl and lower alkynyl, respectively.

As used herein, "aryl" includes "aryl" and "substituted aryl." Thus "aryl" of this invention means any stable 6- to 14-membered monocyclic, bicyclic or tricyclic ring, containing at least one aromatic carbon ring, for example, phenyl, naphthyl, indanyl, tetrahydronaphthyl (tetralin) and the like. The presence of substitution on the aryl group is optional, but when present, the substituents can be halo, alkyl, alkoxy, hydroxy, carboxy, carboxyalkyl, amino, cyano, nitro, trifluoromethyl, acylamino or carbamoyl.

As used herein, the term "heteroaryl" includes "heteroaryl" and "substituted heteroaryl." Thus "heteroaryl" of this invention means a stable 5- to 10-membered monocyclic or bicyclic heterocyclic ring which is aromatic, and which consists of carbon atoms and from 1 to 3 heteroatoms selected from the group consisting of N, O and S and wherein the nitrogen may optionally be quaternized, and including any bicyclic group in which any of the above-defined heteroaryl rings is fused to a benzene ring. The heteroaryl ring may be attached to its pendant group at any heteroatom or carbon atom which results in a stable structure. The presence of substitution on the heteroaryl group is optional and can be on a carbon atom, a nitrogen atom or other heteroatom if the resulting compound is stable and all the valencies of the atoms have been satisfied. When present, the substituents of the substituted heteroaryl groups are the same as for the substituted aryl groups and also include alkylammonium salts when the substituent is an alkyl group attached to the nitrogen atom of the heteroaryl ring. These quartemized ammonium salts include halides, hydrohalides, sulfates, methosulfates, methanesulfonates, toluenesulfates, nitrates, phosphates, maleates, acetates, lactates or any other pharmaceutically acceptable salt. Examples of heteroaryl groups include, but are not limited to, pyddyl, pyrimidinyl, furanyl, thienyl, pyrrolyl, pyrazolyl, imidazolyl, tetrazolyl, benzofuranyl, benzothienyl, indolyl, indolenyl, quinolinyl, isoquinolinyl and benzimidazolyl.

As used herein, "aralkyl" and "heteroaralkyl" refer to an aryl or heteroaryl group attached to an alkyl group. The aryl and heteroaryl groups of this moiety can optionally be substituted in accordance with the definitions herein. Examples of heteroaralkyl groups include but are not limited to 2-, 3-, or 4-pyridylmethyl and 3-(2-, 3- or 4- pyridyl) propyl and the like.

The term "substituted", as used herein, means that one or more hydrogens on the designated atom are replaced with a selection from the indicated groups, provided that the designated atom's normal valency is not exceeded, and that the substitution results in a stable compound.

The substituents of the invention include, as indicated, halo, hydroxy, alkyl, alkoxy, amino, trifluoromethyl, aryl, heteroaryl, monoalkylamino, dialkylamino, trialkylammonium and salts thereof, carbamoyl, acylamino, arylcarbonylamino, alkoxycarbonylamino, carboxy, carboxyalkyl, formamido, guanidino, ureido, sulfamyl, and alkylsulfonamido. These groups can be substituents for alkyl, alkenyl, alkynyl, cycloalkyl, aryl, aralkyl, heteroaryl and heteroaralkyl groups as indicated in accordance with the invention. A "halo" group is a halogen, and includes fluoro, chloro, bromo and iodo groups. The term "alkoxy" refers to an alkyl group having at least one oxygen substituent represented by R—O—. The group "acylamino" is represented by the formula R—C(O)—NH— where R is alkyl. "Arylcarbonylamino" and "alkoxycarbonylamino" are similar to acylamino except that the R is aryl or alkoxy, respectively.

As used herein, "therapeutically-effective amount" refers to that amount necessary to administer to a patient or to cells to achieve an anti-tumor effect; to induce differentiation and/or inhibition of proliferation of malignant cancer cells, benign tumor cells or other proliferative cells; to aid in the chemoprevention of cancer; to promote wound healing; to treat a gastrointestinal disorder; to treat a blood disorder or increase the hemoglobin content of blood; to modulate an immune response; to enhance gene expression; modulate or augment expression of tumor suppressor genes; to enhance insulin expression; to enhance chloride channel expression; to induce tolerance to an antigen; to treat, prevent or ameliorate protozoan infection; or to inhibit histone deacetylase in cells. Methods of determining therapeutically-effective amounts are well known.

When the therapeutic or effective amount of the compound is for treating, preventing or ameliorating cancer or other proliferative disorder, then that amount may be an amount effective to inhibit histone deacetylase in the subject, patient or cancerous cells. Similarly, when the therapeutic or effective amount of the compound is for treating, preventing, or ameliorating protozoan infection then that amount may be an amount effective to inhibit protozoan histone deacetylase in the subject, patient or cancerous cells.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids, and the like. Pharmaceutically acceptable salts include, but are not limited to, hydrohalides, sulfates, methosulfates, methanesulfonates, toluenesulfonates, nitrates, phosphates, maleates, acetates, lactates, arginine salts and lysine salts and the like.

Pharmaceutically-acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences,* 17th ed., Mack Publishing Company, Easton, Pa, 1985, p. 1418, the disclosure of which is hereby incorporated by reference in its entirety.

The "pharmaceutical agents" for use in the methods of the invention related to the coadministration of compounds of Formula I, include but are not limited to anticancer agents as well as differentiating agents. For example, the pharmaceutical agent can be a cytokine, an interleukin, an anti-cancer agent, a chemotherapeutic agent, an antibody, a conjugated antibody, an immune stimulant, an antibiotic, a hormone antagonist or a growth stimulant. The pharmaceutical agent can also be a cytotoxic agent. Cytotoxic agents include antiviral nucleoside antibiotics such as ganciclovir, acyclovir, and famciclovir. Cytotoxic agents can also include radiation therapy.

As used herein, the "chemotherapeutic agents" include but are not limited to alkylating agents, purine and pyrimidine analogs, vinca and vinca-like alkaloids, etoposide and etoposide-like drugs, corticosteroids, nitrosoureas, antimetabolites, platinum-based cytotoxic drugs, hormonal antagonists, anti-androgens and antiestrogens.

The "cytokines" for use herein include but are not limited to interferon, preferably α, β or γ interferon, as well as IL-2, IL-3, G-CSF, GM-CSF and EPO.

As used herein, an "immune stimulant" is a substance such as C. parvum or sarcolectin which stimulates a humoral or cellular component of the immune system.

The chemotherapeutic agents of the invention include but are not limited to tamoxifen, doxorubicin, L-asparaginase, dacarbazine, amsacrine, procarbazine, hexamethylmelamine, mitoxantrone and gemcitabine.

SYNTHETIC METHODS

The compounds of the present invention can generally be prepared by any method known in the art. For example, the compounds of the invention can be made by reacting the acid form of the RCOOH with a reagent of Formula II (Formula II)

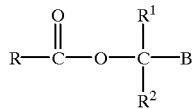

where B is a leaving group such as halogen, methanesulfonate or p-toluenesulfonate and R, $R^1$ and $R^2$ are as defined herein above, with a base or salt, such as a silver or trialkylammonium salt of a reagent of the formula III (Formula II)

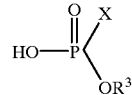

wherein X and $R^3$ in formula III are as defined herein above.

Alternatively, most of the compounds of the present invention may be made by reacting the acid, RCOOH, with a reagent of Formula IV (Formula IV)

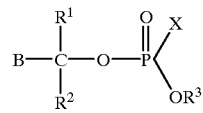

wherein B is a leaving group such a halogen, methanesulfonate or p-toluenesulfonate and R, $R^1$ and $R^2$ are as defined herein above, in the presence of a base or with a salt of the acid, such as a silver or trialkylammonium salt.

In carrying out the synthesis reactions above, it may be desirable to protect certain functional groups, such as amines or hydroxyl groups by the use of standard protecting groups.

Phosphorothioate derivatives can be prepared according to procedures known in the art by reaction of the appropriate compounds, where Z is oxygen, with phosphorus pentasulfide or other sulfurating agent, in the presence of an inert solvent.

The above reagents are readily prepared according to literature procedures; see for example, Nudelman, et al., J. Med. Chem., 35:687–694, 1992; Japanese Patent 07033709 (1995) and Japan Kokai 73 01,133 (1973). The base may be, for example, a trialkylamine, pyridine, an alkali metal carbonate or other suitable base. The reaction may be carried out in the presence or absence of solvent. Suitable solvents include, for example, acetone, benzene, toluene, tetrahydrofuran, ethyl acetate, acetonitrle, dimethylformamide, dimethyl sulfoxide, chloroform, dioxane, 1,2-dichloroethane or in certain instances, water.

The procedures outlined above can be improved by one skilled in the art by, for instance, changing the temperature, duration, stoichiometry or other parameters of the reactions. Any such changes are intended to fall within the scope of this invention.

ACTIVITY

The activities of the compounds of the invention may be measured using generally-accepted techniques known to those skilled in the art consistent with the activity of interest. For example, the activity of compounds useful as differentiating agents can be measured using standard methodology of the nitro-blue tetrazolium reduction assay (e.g., Rabizadeh et al., *FEBS Lett.* 328:225–229, 1993; Chomienne et al., *Leuk. Res.* 10:631, 1986; and Breitman et al. in *Methods for Serum-free Culture of Neuronal and Lymphoid Cells*, Alan R. Liss, NY, p. 215–236, 1984, which are hereby incorporated by reference in their entirety) and as described below. This in vitro assay has been deemed to be predictive and in fact correlative with in vivo efficacy (Castaigne et al., *Blood* 76:1704–1709, 1990).

Another assay which is predictive of differentiating activity is the morphological examination for the presence of Auer rods and/or specific differentiation cell surface antigens in cells collected from treatment groups, as described in Chomienne et al., (*Blood* 76:1710–1717, 1990 which is hereby incorporated by reference in its entirety) and as described below.

The compounds of the present invention also have anti-proliferative and anti-tumor activity. The anti-proliferation activity of compounds of the present invention may be determined by methods generally known to those skilled in the art. Generally-accepted assays for measuring viability and anti-proliferative activity are the trypan blue exclusion test and incorporation of tritiated thymidine, also as described by Chomienne, et al., above, which is incorporated herein by reference. Other assays which predict and correlate antitumor activity and in vivo efficacy are the human tumor colony forming assay described in Shoemaker et al., *Can. Res.* 45:2145–2153, 1985, and inhibition of telomerase activity as described by Hiyayama et al., *J. Natl. Cancer Inst.* 87:895–908, 1995, which are both incorporated herein by reference in their entirety. These assays are described in further detail below.

Cell Cultures

Human promyelocytic leukemia cells (HL-60), human pancreatic carcinoma cells (PaCa-2) and human breast adenocarcinoma cells, pleural effusion cells (MCF-7) can be cultured as follows. Cells are grown in RPMI medium with 10% FCS, supplemented with 2 mM glutamine and incubated at 37° C. in a humidified 5% $CO_2$ incubator. Alternatively, cells can be grown in any other appropriate growth medium and conditions which supports the growth of the cell line under investigation. Viability can be determined by trypan blue exclusion. Cells are exposed to a test compound, cultures are harvested at various time points following treatment and stained with trypan blue.

Cellular Staining to Detect Differentiation

Lipid staining and/or immunochemical staining of casein can be used as a marker for cellular differentiation of breast cancer cells (Bacus et al., *Md. Carcin.* 3:350–362, 1990). Casein detection can be done by histochemical staining of breast cancer cells using a human antibody to human casein as described by Cheung et al., *J. Clin. Invest.* 75:1722–1728, which is incorporated by reference in its entirety.

Nitro-Blue Tetrazolium (NBT) Assay:

Cell differentiation of myeloid leukemia cells can be evaluated, for example, by NBT reduction activity as follows. Cell cultures are grown in the presence of a test compound for the desired time period. The culture medium is then brought to 0.1% NBT and the cells are stimulated with 400 mM of 12-O-tetradecanoyl-phorbol-13-acetate (TPA). After incubation for 30 minutes at 37° C., the cells are examined microscopically by scoring at least 200 cells. The capacity for cells to reduce NBT is assessed as the percentage of cells containing intracellular reduced black formazan deposits and corrected for viability.

Cell Surface Antigen Immunophenotyping

Cell surface antigen immunotyping can be conducted using dual-color fluorescence of cells gated according to size. The expression of a panel of antigens from early myeloid (CD33) to late myeloid can be determined as described in Warrell, Jr. et al., *New Engl. J. Med.* 324:1385–1392, 1992, which is incorporated by reference herein in its entirety.

Apoptosis Evaluation

Apoptosis can be evaluated by DNA fragmentation, visible changes in nuclear structure or immunocytochemical analysis of Bcl-2 expression.

DNA fragmentation can be monitored by the appearance of a DNA ladder on an agarose gel. For example, cellular DNA is isolated and analyzed by the method of Martin et al., *J. Immunol.*, 145:1859–1867, 1990 which is incorporated by reference herein in its entirety.

Changes in nuclear structure can be assessed, for example, by acridine orange staining method of Hare et al., *J. Hist. Cyt.*, 34:215–220, 1986, which is incorporated by reference herein in its entirety.

Immunological detection of Bcl-2 can be performed on untreated cells and cells treated with the test compound. HL-60 cells are preferred but other cell lines capable of expressing Bcl-2 can be used. Cytospins are prepared and the cells are fixed with ethanol. Fixed cells are reacted overnight at 4° C. with the primary monoclonal antibody, anti-Bcl-2 at a dilution of 1:50. Staining is completed to visualize antibody binding, for example, using Strep A-B Universal Kit (Sigma) in accordance with the manufacturer's instructions. Identically-treated cells which received no primary antibody can serve as a non-specific binding control. Commercial kits are also available and can be used for detecting apoptosis, for example, Oncor's Apop Tag®.

Modulation of Gene Expression

The levels of expression from oncogene and tumor suppressor genes can be evaluated by routine methods known in the art such as Northern blotting of RNA, immunoblotting of protein and PCR amplification.

Mouse Cancer Model

Compounds may be examined for their ability to increase the life span of animals bearing B16 melanomas, Lewis lung carcinomas and myelomonocytic leukemias as described in Nudelman et al., *J. Med. Chem.* 35:687–694, 1992, or Rephaeli et al., *Int. J. Cancer* 49:66–72, 1991, which are incorporated by reference herein in their entireties.

For example, the efficacy of compounds of the present invention in a leukemia model can be tested as follows: Balbic mice are injected with WEHI cells and a test compound or control solution is administered the following day. The life span of the treated animals is compared to that of untreated animals.

The efficacy of compounds of the present invention on primary tumors can also be tested with subcutaneously implanted lung carcinoma or B16 melanoma by measuring the mass of the tumor at the site of implantation every two weeks in control and treated animals.

The efficacy of compounds in xenografts can be determined by implanting the human tumor cells subcutaneously into athymic mice. Human tumor cell lines which can be used include, but are not limited to, prostate carcinoma (human Pc-3 cells), pancreatic carcinoma (human Mia PaCa cells), colon adenocarcinoma (human HCT-15 cells) and mammary adenocarcinoma (human MX-I cells). Treatment with control solution or a test compound of the invention begins, for example, when tumors are approximately 100 mg. Anti-tumor activity is assessed by measuring the delay in tumor growth, and/or tumor shrinking and/or increased survival of the treated animals relative to control animals.

Telomerase Activity

A high level of telomerase activity is associated with the high proliferation rate found in cancer cells. Compounds which inhibit telomerase activity result in inhibition of cancer cell growth and de-differentiation. Commercially available telomerase assays may be used to assess the anticancer activities of compounds on cancer cell lines.

Chemoprevention

The chemoprevention activity of the compounds of the invention can be determined in the two-stage mouse carcinogenesis model of Nishimo et al. (supra).

Assay of Compounds

Compounds of the invention, their salts or metabolites, may be measured in a biological sample by any method known to those skilled in the art of pharmacology, clinical chemistry or the like. Such methods for measuring these compounds are standard methods and include, but are not limited to high performance liquid chromatography (HPLC), gas chromatography (GC), gas chromatography mass spectroscopy (GC-MS), radioimmunoassay (RIA), and others.

Dosage and Formulation

The compounds of the present invention may be administered to a mammalian patient to treat cancer or may be administered in any other method of the invention which involves treating a patient by any means that produces contact of the active agent with the agent's site of action in the body of the subject. Mammalian patients include humans and domestic animals. The compounds of the invention may be administered by any conventional means available for use in conjunction with pharmaceuticals, either as individual therapeutic agents or in a combination of therapeutic agents. The compounds can be administered alone, but are generally administered with a pharmaceutical carrier selected on the basis of the chosen route of administration and standard pharmaceutical practice. The pharmaceutical compositions of the invention may be adapted for oral, parenteral, transdermal, transmucosal, rectal or intranasal administration, and may be in unit dosage form, as is well known to those skilled in the pharmaceutical art. The term "parenteral" as used herein includes subcutaneous, intravenous, intramuscular, or intrasternal injection or infusion techniques.

The appropriate dosage administered in any given case will, of course, vary depending upon known factors, such as the pharmacodynamic characteristics of the particular agent and its mode and route of administration; the age, general health, metabolism, weight of the recipient and other factors which influence response to the compound; the nature and extent of the symptoms; the kind of concurrent treatment; the frequency of treatment; and the effect desired. A daily dosage of active ingredient can be expected to be about 10 to 10,000 milligrams per meter$^2$ of body mass (mg/m$^2$), with the preferred dose being 50–5,000 mg/m$^2$ body mass.

Dosage forms (compositions suitable for administration) contain from about 1 mg to about 1 g of active ingredient per unit. In these pharmaceutical compositions the active ingredient will ordinarily be present in an amount of about 0.5–95% by weight based on the total weight of the composition.

The active ingredient may be administered orally in solid or semi-solid dosage forms, such as for example hard or soft-elatin capsules, tablets, and powders, or in liquid dosage forms, such as elixirs, syrups, disperse powders or granules, emulsions, and aqueous or oily suspensions. It can also be administered parenterally, in sterile liquid dosage forms. Other dosage forms include transdermal administration via a patch mechanism or ointment.

Compositions intended for oral use may be prepared according to any methods known to the art for the manufacture of pharmaceutical compositions and such compositions may contain one or more agents including sweetening agents, flavoring agents, coloring agents, and preserving agents in order to provide a pharmaceutically elegant and palatable preparation.

Tablets contain the active ingredient in admixture with non-toxic pharmaceutically acceptable excipients which are suitable for the manufacture of tablets. Such excipients may include, for example, inert diluents, such as calcium phosphate, calcium carbonate, sodium carbonate, sodium phosphate, or lactose; granulating disintegrating agents, for example, maize starch or alginic acid; binding agents, such as starch, gelatin, or acacia; and lubricating agents, for example, magnesium stearate, steario acids or talc. Compressed tablets may be uncoated or may be sugar coated or film coated by known techniques to mask any unpleasant taste and protect the tablet from the atmosphere, or enteric coated for selective disintegration and adsorption in the gastrointestinal tract.

Hard gelatin capsules or liquid filled soft gelatin capsules contain the active ingredient and inert powdered or liquid carriers, such as, but not limited to calcium carbonate, calcium phosphate, kaolin, lactose, lecithin starch, cellulose derivatives, magnesium stearate, stearic acid, arachis oil, liquid paraffin, olive oil, pharmaceutically-accepted synthetic oils and other diluents suitable for the manufacture of capsules. Both tablets and capsules can be manufactured as sustained release-products to provide for continuous release of medication over a period of hours.

Aqueous suspensions contain the active compound in admixture with excipients suitable for the manufacture of aqueous suspensions. Such excipients are suspending agents, e.g., sodium carboxymethylcellulose, methylcellulose, hydroxypropylmethylcellulose, sodium alginate, polyvinylpyrrolidone, gum tragacanth, and gum acacia; dispersing or wetting agents, such as a naturally occurring phosphatide, e.g., lecithin, or condensation products of an alkylene oxide with fatty acids, for example of polyoxyethylene stearate, or a condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersable powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, such as glycerol, sorbitol or sucrose. Such formulations may also contain a demulcent, a preservative and flavoring and coloring agents.

The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, for example, as a solution in 1,3-butanediol.

In general, water, a suitable oil, saline, aqueous dextrose (glucose), polysorbate and related sugar solutions, emulsions, such as Intralipid® (Cutter Laboratories, Inc., Berkley Calif.) and glycols such as propylene glycol or polyethylene glycols are suitable carriers for parenteral solutions. Antioxidizing agents, such as but not limited to sodium bisulfite, sodium sulfite, or ascorbic acid, either alone or combined, are suitable stabilizing agents. Also used can be citric acid and its salts and sodium EDTA. In addition, parenteral solutions can contain preservatives, such as but not limited to benzalkonium chloride, methyl- or propylparaben, and chlorobutanol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc., with appropriate excipients. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

Suitable pharmaceutical carriers are described in *Remington's Pharmaceutical Sciences*, Mack Publishing Company, a standard reference text in this field, which is incorporated herein by reference in its entirety.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entirety.

EXAMPLE 1

SYNTHESIS OF BUTYROYLOXYMETHYL DIETHYL PHOSPHATE

(COMPOUND 1)

The synthesis of butyroyloxymethyl diethyl phosphate (BODP) was carried out as follows: Triethylamine ($Et_3N$)(5 ml, 1.2 eq) was added dropwise to a stirred solution of diethyl phosphate (4.1 g, 30 mmol) and chloromethyl butyrate (4.12 g, 1 eq) in dry dimethylformamide (DMF) (10 mL), at room temperature under nitrogen. The reaction mixture was heated at 65° C. for three hours whereby a large amount of precipitate formed and thin layer chromatography (TLC: $CHCl_3$:MeOH 7:1, detection-vanillin) showed that most of the acid had reacted. The precipitate was filtered and washed with ethyl acetate. The filtrate was partitioned between water and ethyl acetate. The aqueous phase was extracted back with a small amount of ethyl acetate, and the combined organic phase was washed three times with water, three times with a 5% solution of sodium carbonate ($NaHCO_3$) and twice with brine, dried with magnesium sulfate ($MgSO_4$) and evaporated to give the crude product as a yellowish material (1.6 g, 65% yield) which was chromatographed on silica gel (60 g, ethyl acetate:hexane:isopropanol 8:8:1). The product was found in the second fraction. The pure product (1 g, 40% yield) was a colorless oil.

Additional compounds of the invention are provided in Table I. These compounds are those of Formula I having the designated groups. These compounds may be synthesized in a manner analogous to the method of Example 1 or as provided in the Detailed Description of the Invention.

TABLE 1

$$A-P\overset{Z}{\underset{OR^3}{\lessgtr}}X \quad \text{wherein } A = R-\overset{O}{\overset{\|}{C}}-O-\overset{R^1}{\underset{R^2}{C}}-O-$$

[A]

| R | $R^1$ | $R^2$ | Z | X | $R^3$—O— |
|---|---|---|---|---|---|
| n-$C_3H_7$ | H | H | O | $C_2H_5O$ | $CH_2$=CH—$CH_2$—O— |
| n-$C_3H_7$ | $CH_3$ | H | O | 2-Ethylhexyl-O— | 2-Ethylhexyl-O— |
| n-$C_3H_7$ | $CH_3$ | H | O | $C_6H_5CH_2O$— | $C_6H_5CH_2O$— |
| i-$C_3H_7$ | H | H | O | $C_2H_6$ | $C_2H_5O$ |
| $CH_2$=$CHCH_2$ | H | H | S | $C_2H_5O$ | $C_2H_5O$ |
| 2-Py-$C_3H_6$ | $CH_3$ | $CH_3$ | O | $CH_3O$ | $CH_3O$ |
| 3-Cl-$C_3H_6$ | n-$C_3H_7$ | H | S | $C_6H_5CH_2O$ | $C_6H_5O$ |
| n-$C_3H_7$ | $C_2H_5$ | H | S | n-$C_3H_7O$ | $C_2H_5O$ |
| $C_6H_5CH_2$ | 2-$CH_3OCH_2CH_2$ | H | O | $(CH_3)_2NCH_2CH_2O$ | $(CH_3)_2NCH_2CH_2O$ |
| 4-$C_6H_5(CH_2)_3$ | $CH_2$=$CHCH_2$ | H | O | $C_6H_5CH_2O$ | $C_6H_5CH_2O$ |
| n-$C_3H_7$ | $CH_3$ | H | O | $C_2H_5O$ | $C_2H_5O$ |

EXAMPLE 2

CLONOGENICITY OF ESTABLISHED TUMOR CELL LINES

Inhibition of tumor growth was tested using cell lines as follows:

The cell lines listed in Table 2 were grown to 70–80% confluence in complete medium (RPMI 1640 containing 10% fetal calf serum (FCS), 100 IU penicillin, 100 µg/mL streptomycin and 2 mM L-glutamine). Cells were harvested, washed in complete medium and counted. Cell viability was determined by trypan blue exclusion. The cells were placed into soft agar (0.12% in media) and plated at 5,000 viable cells per well onto an agarose underlayer (0.4%) in 24-well plates. After overnight culture, AB or BODP was added at the indicated concentration. Control cells received media alone. As a control for cell death, cells were treated with a superlethal dose of 10 µg/ml of cisplatin. The dosage of AB or BODP which inhibited fifty percent or ninety percent of cell proliferation ($IC_{50}$ or $IC_{90}$ respectively) was calculated using the Chou Analysis' Median Effective Dose equation.

Figure 1B:
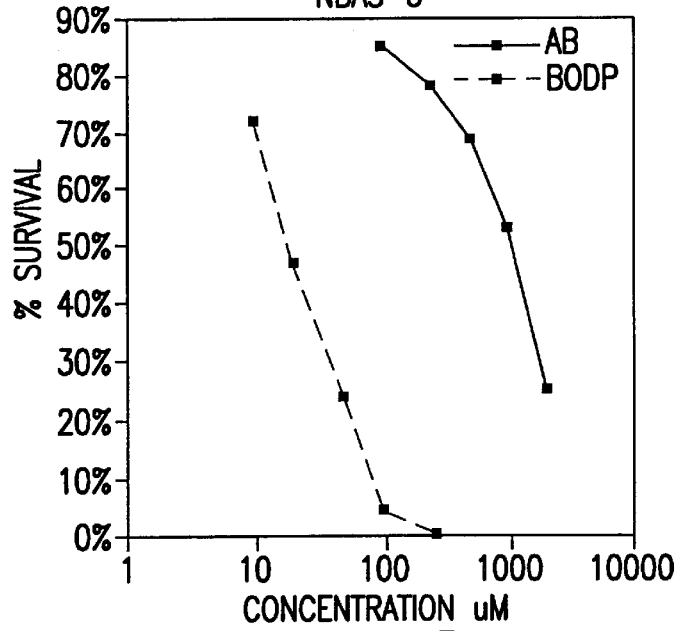
Figure 1C:
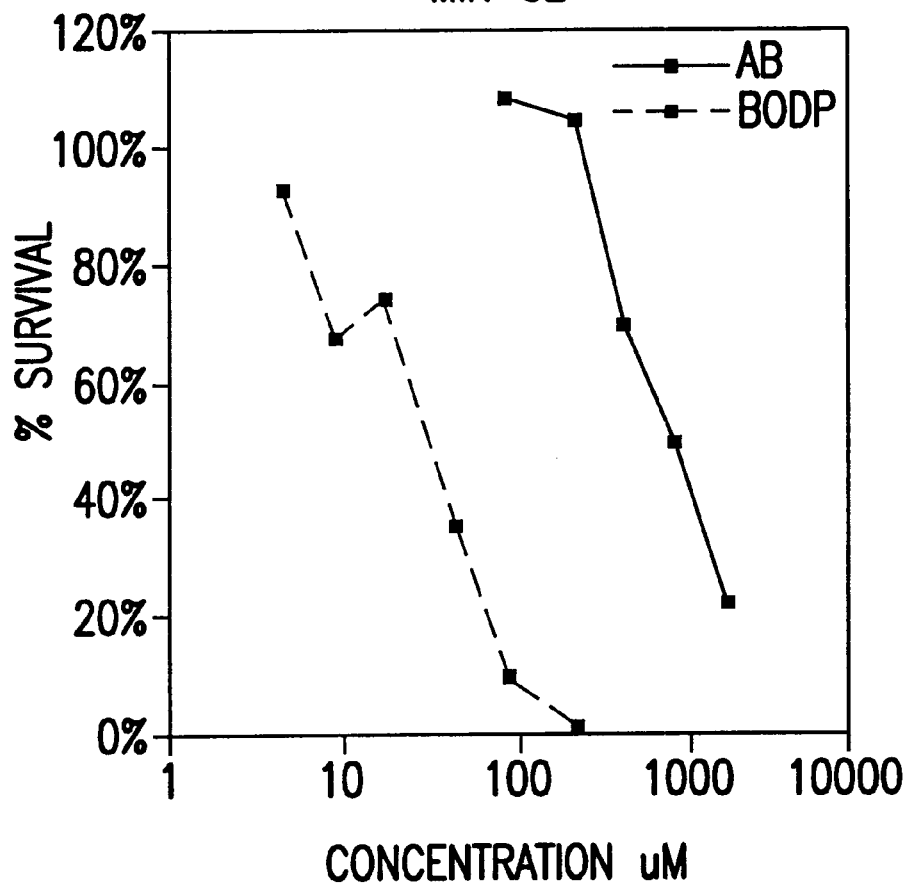

Clonogenicity is determined as the percentage of clones in treated cultures relative to clones in mediumun-treated control cultures. A representative clonogenicity titration curve for each of AB and BODP is shown with four neuroblastoma cell lines in FIG. 1. The $IC_{50}$ and $IC_{90}$ values of AB and BODP for cancer cell lines are provided in Table 3.

The results demonstrate that BODP is a more potent growth inhibitor than AB. The data show that BODP and AB inhibit cell proliferation in a dose-dependent manner but that the cells are at least an order of magnitude more sensitive to BODP. The ratio of $IC_{50}$ AB:$IC_{50}$ BODP ranges between 5.8 to 66-fold with a median value of 25.2 $\mu$M. Similarly the ratio of $IC_{90}$ AB:$IC_{90}$ BODP ranges between 9.1 to 183.5 with a median value of 28.75 $\mu$M.

These results demonstrate that BODP is a significantly more potent tumor cell clonogenicity inhibitor than AB. The difference between AB and BODP is even more pronounced when the $IC_{90}$ is compared. The $IC_{90}$ values are clinically important for assessing eradication of residual cancer disease.

TABLE 2

HUMAN TUMOR CELL LINES

| CELL LINES | ORIGIN |
| --- | --- |
| MCF7-WT | Breast Carcinoma |
| MCF7-40F | Breast Carcinoma |
| PC3 | Prostate Carcinoma |
| LNCaP | Prostate Carcinoma |
| K-562 | Erythroleukemia |
| SK-N-SH | Neuroblastoma |
| NBAS-5 | Neuroblastoma |
| IMR-32 | Neuroblastoma |
| LA1-5S | Neuroblastoma |
| NBL-W-N | Neuroblastoma |
| SMS-KAN | Neuroblastoma |
| NGP | Neuroblastoma |
| SK-N-MC | Neuroblastoma |
| SMS-KCN | Neuroblastoma |

TABLE 3

INHIBITION OF ESTABLISHED AND PRIMARY TUMOR CELL LINES BY AB AND BODP

| | AB | | BODP | | Ratio AB/BODP | |
| --- | --- | --- | --- | --- | --- | --- |
| Cell Line | $IC_{50}$[a] | $IC_{90}$ | $IC_{50}$ | $IC_{90}$ | $IC_{50}$ | $IC_{90}$ |
| SK-N-SH | 998 | 3397 | 15 | 44 | 66.5 | 77.2 |
| NBAS-5 | 883 | 13030 | 21 | 71 | 42 | 183.5 |
| SK-N-MC | 215 | 1314 | 37 | 145 | 5.8 | 9.1 |
| IMR-32 | 881 | 3566 | 35 | 88 | 25.2 | 40.5 |
| NGP | 197 | 1622 | 17 | 49 | 11.6 | 33.1 |
| LA1-5S | 1627 | 2675 | 38 | 105 | 42.8 | 25.5 |
| SMS-KCN | 1872 | NA | 54 | NA | 34.7 | NA |
| NBL-W-N | 489 | 3074 | 38 | 96 | 12.9 | 32 |
| SMS-KAN | 1138 | 2079 | 45 | 128 | 25.3 | 16.2 |

[a]All concentrations are in $\mu$M.

EXAMPLE 3

INHIBITION OF HUMAN CLONOGENICITY OF HUMAN PANCREATIC CELLS

The effect of 24 hour exposure to BODP or AB was determined by a colony-forming assay on the pancreatic cell line, BxPC-3, which is a primary adenocarcinoma (ACTTnr:CRL-1687). Freshly trypsinized cells were plated at 500 cells/dish in 60 mm$^2$ tissue culture dishes with the indicated concentration of each compound and incubated for 24 hours at 37° C. in 5% $CO_2$/air atmosphere. The cultures were washed with PBS, fresh medium was added, and the cultures were incubated for 7–12 days to allow the formation of colonies. Colonies were fixed with methanol, stained with Giemsa and counted. All incubations were performed in triplicate.

Figure 2:
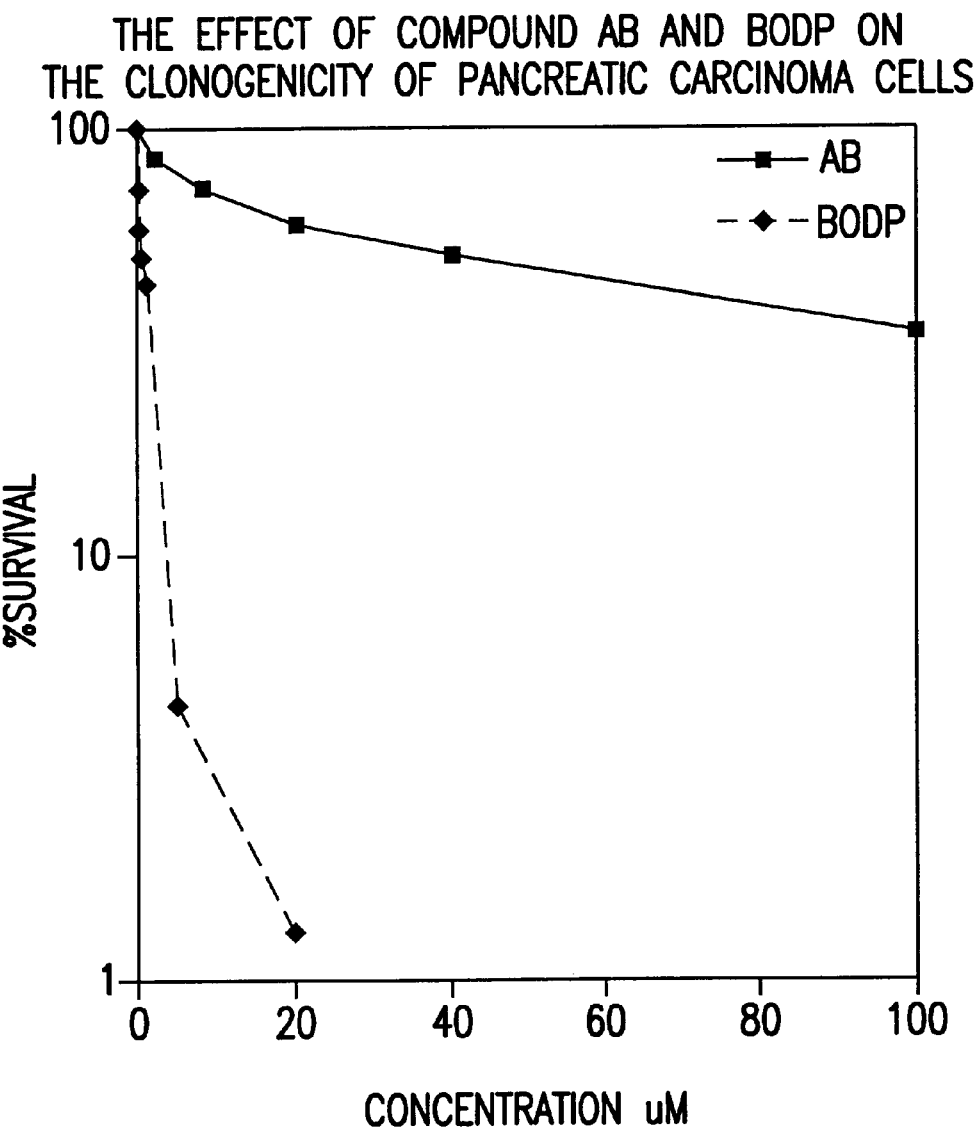
FIG. 2 is a graphic illustration showing the in vitro effect of BODP and AB on the differentiation of HL-60 cells.

The results shown in FIG. 2 demonstrate that 24 hour treatment with BODP caused a dose-ependent growth inhibition, with complete inhibition occurring at concentrations above 50 $\mu$M. In contrast, a 100 $\mu$M dose of AB did not cause complete growth inhibition of the cells.

EXAMPLE 4

INDUCTION OF DIFFERENTIATION

Cancer cell differentiation was evaluated in a human leukemia cell line by nitroblue tetrazolium reduction (NBT) activity (Koeffier, *Blood,* 62: 709–721, 1983) or by changes in expression of myelocytic maturation marker CD11b. Differentiation was also evaluted in a breast carcinoma cell line by lipid staining (Bacus et al., *Mol. Carcinog.* 3:350–362, 1990).

Figure 3:
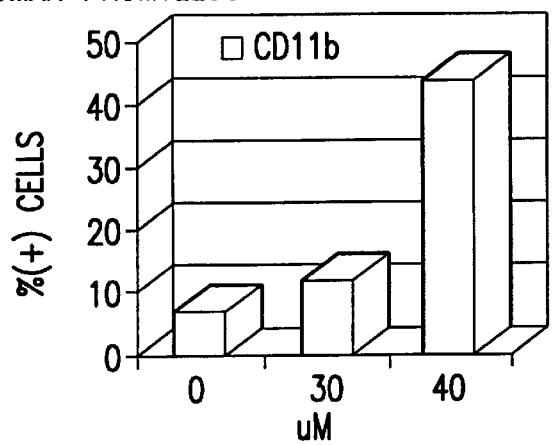
FIG. 3 is a bar graph showing the effect of BODP and AB on the expression of CD11b in human promyelocytic leukemic cell line HL-60.

The level of CD11b was measured on HL-60 cells by flow cytometry using a monoclonal antibody (MAb) against CD11b in a standard indirect immunofluorescence assay. Cells were cultured for three or six days with the indicated concentration of BODP. Cultured cells were collected by centrifugation, resuspended at $10^6$ cells per 20 $\mu$l RPMI+ 10% FCS and incubated with MAb for 30 minutes at 4° C. The cells were washed twice in cold PBS+10% FCS and incubated with a 1:20 dilution of FITC-conjugated F(ab')$^2$ fragment of rabbit anti-mouse IgG for 20–30 minutes at 4° C. in the dark. After washing the cells twice in cold PBS+10% FCS, flow cytometry was performed on a FACSstar (Becton Dickson) using an argon ion laser adjusted to excitation wavelength of 488 nm on samples containing $10^4$ cells. The results are shown graphically in FIG. 3. BODP was a more active differentiation inducer compared to AB.

The expression of CD11b increased 7-fold over the expression of untreated cells when the cells were exposed to 40 $\mu$M BODP for four days. At the same concentration of AB there was no increase in CD11b. At 175-fold higher concentration of AB (800 $\mu$M) increased the expression of CD11b to 12%, which is only 1.74-fold above the basal level expressed in untreated cells.

EXAMPLE 5

INDUCTION OF HEMOGLOBIN SYNTHESIS

Induction of hemoglobin (Hb) synthesis was measured by two complementary methods.

(1) Hb Measurement: Hemoglobin was measured by benzidine staining of K562 cells after 5 days exposure to BODP or AB according to the procedure of Fibach et al. (1993) infra.

(2) Quantitative measurement of fetal hemoglobin (HbF) in K562 culture or human erythroid cultures was determined by ion-exchange high pressure liquid chromatography (HPLC) as described by Fibach et al., *Blood* 81:1630–1635, 1993.

K562 cells: K562 is an erythroblast cell line (obtained from the ATCC, Rockville, Md.) that develops some properties of erythroid, megakaryocyte or monocyte cells, depending on the specific stimulus, when induced by different chemicals. K562 cells were grown in RPMI medium with 10% FCS, supplemented with 2 mM glutamine. Cells were incubated at 37° C. in a humidified, 5% $CO_2$ incubator.

Figure 4:
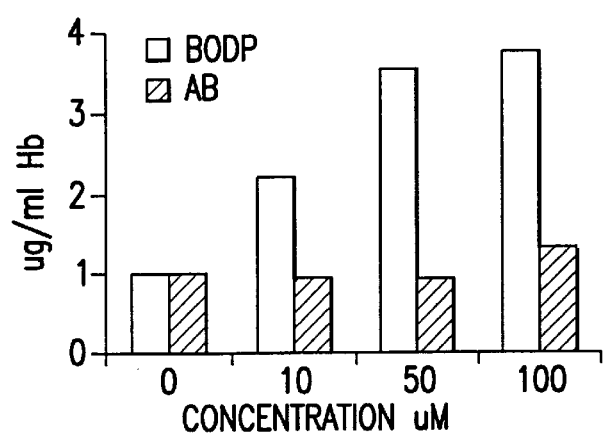
FIG. 4 is a bar graph showing the effect of BODP and AB on hemoglobin accumulation in stained K-562 cells.
Figure 5:
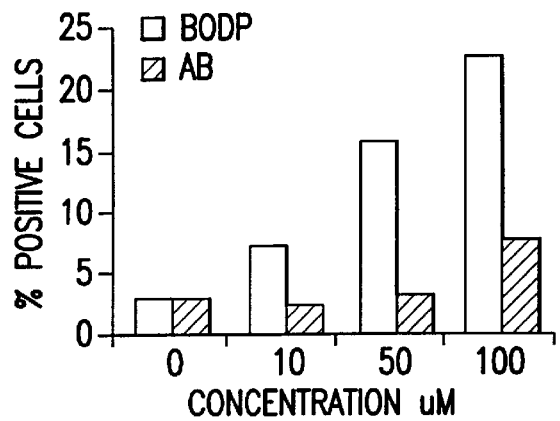
FIG. 5 is a bar graph showing the effect of BODP and AB on hemoglobin accumulation as determined by analysis of culture lysate by HPLC.

Treatment of K562 cells with BODP or AB showed that, on a molar basis, the compound of the invention had higher activity in inducing erythroid differentiation (as measured by hemoglobin accumulation) than did AB. This was evident from the higher proportion of Hb-containing cells per the total cell population (FIG. 4) as well as the total Hb content of the cultures (FIG. 5). The extent of differentiation of the treated cultures was directly related to the drug dose. The diluents, DMF and water, had no effect on cell growth, cell viability or differentiation.

What is claimed is:

1. A compound represented by the formula:

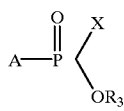

wherein A is

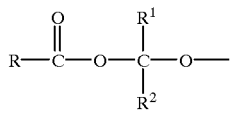

and wherein

R is $C_3$–$C_{10}$ straight chain alkyl, optionally substituted with one amino, acylamino, halo, trifluoromethyl, hydroxy, alkoxy, alkyl, acyl, aryl, heteroaryl or substituted heteroaryl group; or $C_2$–$C_{10}$ alkenyl or $C_2$–$C_{10}$ alkynyl, each optionally substituted with at least one amino, acylamino, halo, trifluoromethyl, hydroxy, alkoxy, alkyl, carbonyl, aryl, heteroaryl, substituted heteroaryl group or combination thereof;

$R^1$ and $R^2$ are each independently H, $C_1$–$C_6$ alkyl, $C_2$–$C_6$ alkenyl or $C_2$–$C_6$ alkynyl wherein the alkyl, alkenyl or alkynyl group or combination thereof is optionally substituted with halo or alkoxy;

X is $R^4$ or $OR^5$, and $R^3$ and $R^5$ are both H or each is independently $C_1$–$C_6$ alkyl, alkenyl, alkynyl, aralkyl, aryl, heteroaryl or heteroaralkyl;

$R^4$ is $C_1$–$C_6$ alkyl, alkenyl, alkynyl, aralkyl, aryl, heteroaryl or heteroaralkyl;

with the proviso that when R is n-propyl and $R^1$ or $R^2$ is H and the other is trichloromethyl, then X is not methoxy and $R^3$ is not methyl.

2. The compound of claim 1 wherein R is $C_3$–$C_6$ alkyl or alkenyl, optionally substituted with halo, alkyl, aryl or heteroaryl; $R^1$ is H or alkyl and $R^2$ is H; and X and —$OR^3$ are each independently alkyloxy, alkenyloxy, alkynyloxy, aryloxy, arylalkyloxy, heteroaryloxy, or heteroarylalkyloxy.

3. The compound of claim 1 wherein said compound is butyroyloxymethyl diethyl phosphate, 1-(1-butyroyloxy) ethyl diethyl phosphate, mono(butyroyloxymethyl) phosphate or 1{1-(4-phenylbutyroyloxy)ethyl} diethyl phosphate.

4. A compound represented by the formula:

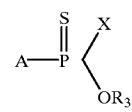

wherein A is

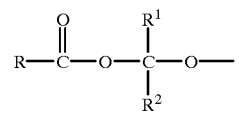

and wherein

R is $C_1$–$C_{10}$ alkyl, $C_2$–$C_{10}$ alkenyl or $C_2$–$C_{10}$ alkynyl, each optionally substituted with at least one amino, acylamino, halo, trifluoromethyl, hydroxy, alkoxy, alkyl, acyl, aryl, heteroaryl, substituted heteroaryl group or combination thereof;

$R^1$ and $R^2$ are each independently H or $C_1$–$C_6$ alkyl, $C_2$–$C_6$ alkenyl or $C_2$–$C_6$ alkynyl wherein the alkyl, alkenyl or alkynyl group or combination thereof is optionally substituted with halo or alkoxy;

X is A, $R^4$ or $OR^5$, wherein $R^3$ and $R^5$ are both H or each is independently $C_1$–$C_6$ alkyl, alkenyl, alkynyl, aralkyl, aryl, heteroaryl or heteroaralkyl; and $R^4$ is $C_1$–$C_6$ alkyl, alkenyl, alkynyl, aralkyl, aryl, heteroaryl or heteroaralkyl;

or both X and $OR^3$ are A.

5. A pharmaceutical composition comprising a therapeutically-effective amount of a compound represented by the formula:

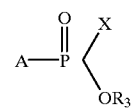

wherein A is

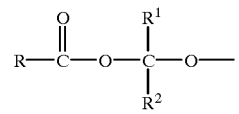

and wherein

R is $C_3$–$C_{10}$ straight chain alkyl, $C_2$–$C_{10}$ alkenyl or $C_2$–$C_{10}$ alkynyl, each optionally substituted with at least one amino, acylamino, halo, trifluoromethyl, hydroxy, alkoxy, alkyl, acyl, aryl, heteroaryl, substituted heteroaryl group or combination thereof;

$R^1$ and $R^2$ are each independently H, $C_1$–$C_6$ alkyl, $C_2$–$C_6$ alkenyl or $C_2$–$C_6$ alkynyl, wherein the alkyl, alkenyl or alkynyl group or combination thereof is optionally substituted with halo or alkoxy;

X is $R^4$ or $OR^5$, and $R^3$ and $R^5$ are both H or each is independently $C_1$–$C_6$ alkyl, alkenyl, alkynyl, aralkyl, aryl, heteroaryl or heteroaralkyl;

$R^4$ is $C_1$–$C_6$ alkyl, alkenyl, alkynyl, aralkyl, aryl, heteroaryl or heteroaralkyl;

with the proviso that when R is n-propyl and $R^1$ or $R^2$ is H and the other is trichloromethyl, then X is not methoxy and $R^3$ is not methyl; and a pharmaceutically acceptable carrier or diluent.

6. The pharmaceutical composition of claim 5 wherein R is C3–C6 alkyl or alkenyl, optionally substituted with halo, alkyl, aryl or heteroaryl; $R^1$ is H or alkyl and $R^2$ is H; X and —$OR^3$ are each independently alkyloxy, alkenyloxy, alkynyloxy, aryloxy, arylalkyloxy, heteroaryloxy, or heteroarylalkyloxy.

7. The pharmaceutical composition of claim 5 wherein said compound is butyroyloxymethyl diethyl phosphate, 1-(1-butyroyloxy)ethyl diethyl phosphate, mono (butyroyloxymethyl) phosphate or 1{1-(4-phenylbutyroyloxy)ethyl} diethyl phosphate.

8. A pharmaceutical compsition comprising a therapeutically effective amount of a compound represented by the formula:

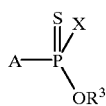

wherein A is

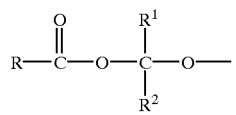

and wherein
R is $C_1$–$C_{10}$ alkyl, $C_2$–$C_{10}$ alkenyl or $C_2$–$C_{10}$ alkynyl, each optionally substituted with at least one amino, acylamino, halo, trifluoromethyl, hydroxy, alkoxy, alkyl, acyl, aryl, heteroaryl, substituted heteroaryl group or combination thereof;

$R^1$ and $R^2$ are each independently H or $C_1$–$C_6$ alkyl, $C_2$–$C_6$ alkenyl or $C_2$–$C_6$ alkynyl wherein the alkyl, alkenyl or alkynyl group or combination thereof is optionally substituted with halo or alkoxy;

X is A, $R^4$ or $OR^5$ wherein
$R^3$ and $R^5$ each is independently H, $C_1$–$C_6$ alkyl, alkenyl, alkynyl, aryl, aralkyl, heteroaryl or heteroaralkyl;
$R^4$ is $C_1$–$C_6$ alkyl, alkenyl, alkynyl, aryl, aralkyl, heteroaryl or heteroaralkyl;
or both X and $OR^3$ are A;
and a pharmaceutically acceptable carrier or diluent.

9. The pharmaceutical composition of claim 5 or 8 further comprising a cytotoxic agent.

10. The pharmaceutical composition of claim 5 or 8 further comprising an antiviral nucleoside antibiotic selected from the group consisting of ganciclovir, acyclovir, and famciclovir.

11. The pharmaceutical composition of claim 10 wherein said antibiotic is ganciclovir.

12. The pharmaceutical composition of claim 5 or 8 further comprising a chemotherapeutic agent selected from the group consisting of alkylating agents, purine and pyrimidine analogs, vinca and vinca-like alkaloids, etoposide and etoposide-like drugs, corticosteroids, nitrosoureas, antimetabolites, platinum based cytotoxic drugs, hormonal antagonists, anti-androgens and antiestrogens.

13. The pharmaceutical composition of claim 5 or 8 further comprising a cytokine.

14. The pharmaceutical composition of claim 13 wherein the cytokine is an interferon.

15. The pharmaceutical composition of claim 5 or 8 further comprising an immune stimulant.

16. The pharmaceutical composition of claim 15 wherein said immune stimulant is *Corynebactedum parvum* or a sarcolectin.

17. A method of treating cancer or other proliferative disorder in a patient which comprises administering to the patient an amount of a compound of any one of claims 1–4 effective to treat the cancer or disorder.

18. The method of claim 17 wherein the disorder is leukemia, squamous cell carcinoma, prostate carcinoma, breast carcinoma, colon carcinoma, pancreatic carcinoma, lug carcinoma, renal carcinoma, neuroblastoma or melanoma.

19. The method of claim 17 wherein said compound is administrated orally, parenterally, transdermally, transmucosally, intranasally, rectally or topically.

20. The method of claim 17 wherein said effective amount is an amount effective to inhibit histone deacetylase in the patient.

21. A method of differentiating or blocking proliferation of cancerous or neoplastic cells comprising administering to said cells a compound of any one of claims 1–4 in an amount effective to cause differentiation of or to block proliferation of said cancerous or neoplastic cells.

22. The method of claim 21 wherein the compound is administered to said cells in vivo.

23. The method of claim 21 wherein the compound is administered to said cells in vitro.

24. The method of claim 21 wherein said compound is administered orally, parenterally, transdermally, transmucosally, intranasally, rectally or topically.

25. A method of enhancing the action of a pharmaceutical agent useful for the treatment of cancer or other proliferative disorder, comprising co-administering to a patient a therapeutically-effective amount of a compound of any one of claims 1–4 and a therapeutically effective amount of said pharmaceutical agent, wherein said pharmaceutical agent is selected from the group consisting of a cytokine, an interleukin, an anti-cancer agent of anti-neoplastic agent, a chemotherapeutic agent, an antibody, a conjugated antibody, an immune stimulant, antibiotic, a hormone antagonist and a growth stimulant.

26. The method of claim 25 wherein said pharmaceutical agent is an antibiotic.

27. The method of claim 25 wherein said antibiotic is selected from the group consisting of ganciclovir, acyclovir, and famciclovir.

28. The method of claim 25 wherein said pharmaceutical agent is a chemotherapeutic agent.

29. The method of claim 27 wherein said pharmaceutical agent is a chemotherapeutic agent selected from the group consisting of an alkylating agent, a purine analog, a pyrimidine analog, a vinca alkaloid, an etoposide, a corticosteroid, a nitrosourea, an antimetabolite, a platinum-based cytotoxic drug, a hormonal antagonist, an anti-androgen and an anti-estrogen.

30. The method of claim 29 wherein said chemotherapeutic agent is selected from the group consisting of tamoxifen, doxorubicin, 1-asparaginase, dacarbazine, amsacrine, procarbazine, hexamethylmelamine, mitoxantrone and gemcitabine.

31. The method of claim 29 wherein said chemotherapeutic agent is an interferon.

32. The method of claim 25 wherein said pharmaceutical agent is an immune stimulant.

33. The method of claim 32 wherein said immune stimulant is *Corynebacterium parvum* or a sarcolectin.

34. The method of claim 27 wherein said chemotherapeutic agent is selected from the group consisting of tamoxifen, doxorubicin, 1-asparaginase, dacarbazine, amsacrine, procarbazine, hexamethylmelamine, mitoxantrone and gemcitabine.

35. The method of claim 25 wherein said compound is administered orally, parenterally, transdermally, transmucosally, intranasally, rectally or topically.

36. A method of ameliorating the effects of a cytotoxic agent in a mammalian patient which comprises administering to the patient a therapeutically-effective amount of said cytotoxic agent and a compound of any one of claims 1–4 for a time and in an amount to induce growth arrest of rapidly-proliferating epithelial cells or bone marrow stem cells of said patient and thereby protecting said cells from cytotoxic effects of said agent.

37. The method of claim 36 wherein said rapidly proliferating epithelial cells are in hair follicles, gastrointestinal tract or bladder of said patient.

38. The method of claim 36 wherein said rapidly-proliferating epithelial cells are hair follicle cells or intestinal cryt cells of said patient.

39. The method of claim 36 wherein said cytotoxic agent and said compound are administered simultaneously.

40. The method of claim 36 wherein said cytotoxic agent is administered prior to or after administration of the compound.

41. The method of claim 36 wherein said cytotoxic agent and said compound are administered systemically or topically.

42. A method of inhibiting telomerase activity in cancer cells which comprises administering to said cells an amount of a compound of any one of claims 1–4 effective to decrease the basal level of telomerase activity in said cells and thereby inhibit malignant progression of said cells.

43. The method of claim 42 wherein said compound is administered to the cells in vivo.

44. The method of claim 43 wherein said compound is administered to the patient orally, parentally, transdermally, transmucosally, intranasally, rectally or topically.

45. The method of claim 42 wherein said compound is administered to the cells in vitro.

46. A method of treating virus-associated tumors which comprises co-administering to a patient a therapeutically-effective amount of a compound of any one of claims 1–4 and a therapeutically-effective amount of an antiviral agent.

47. The method of claim 46 wherein said antiviral agent is ganciclovir, acyclovir, or famciclovir.

48. The method of claim 46 wherein said virus-associated tumor is an EBV-associated malignancy, Kaposi's sarcoma, an AIDS-related lymphoma, a hepatitis B-associated malignancy or a hepatitis C-associated malignancy.

49. The method of claim 46 wherein said EBV-associated malignancy is nasopharyngeal carcinoma or non-Hodgkin's lymphoma.

50. The method of claim 46 wherein said compound is administered orally, parenterally, transdermally, transmucosally, intranasally, rectally or topically.

51. A method of treating cancer or other proliferative disorder in a patient in need of such treatment which comprises administering to the patient a compound of any one of claims 1–4 in an amount effective to induce cellular apoptosis of the cancer cells or of the cells of the proliferative disorder.

52. The method of claim 51 wherein said compound is administered orally, parenterally, transdermally, transmucosally, intranasally, rectally or topically.

* * * * *

UNITED STATES PATENT AND TRADEMARK OFFICE
CERTIFICATE OF CORRECTION

PATENT NO. : 6,030,961
DATED : February 29, 2000
INVENTOR(S) : Abraham NUDELMAN and Ada REPHAELI It is certified that error appears in the above-identified patent and that said Letters Patent is hereby corrected as shown below:

On the first page, item [73] Assignees, should read - - Beacon Laboratories, Inc., Phoenix, Maryland; Bar-Ilan University, Ramat-Gan, Israel; and Mor Research Applications, Ltd., Givat Shmuel, Israel - -.

Signed and Sealed this

Nineteenth Day of September, 2000

*Attest:*

Q. TODD DICKINSON

*Attesting Officer*  *Director of Patents and Trademarks*